United States Patent
Bingham et al.

(12) 
(10) Patent No.: US 6,331,559 B1
(45) Date of Patent: *Dec. 18, 2001

(54) LIPOIC ACID DERIVATIVES AND THEIR USE IN TREATMENT OF DISEASE

(75) Inventors: Paul M. Bingham; Zuzana Zachar, both of Centereach, NY (US)

(73) Assignee: The Research Foundation of State University of New York at Stony Brook, Stony Brook, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/427,477

(22) Filed: Oct. 26, 1999

Related U.S. Application Data

(60) Provisional application No. 60/105,628, filed on Oct. 26, 1998.

(51) Int. Cl.[7] ............ A61K 31/385; A61K 31/185; C07D 339/02

(52) U.S. Cl. ............ 514/440; 514/578; 549/39; 562/147

(58) Field of Search .............. 549/39; 514/440, 514/578; 562/147

(56) References Cited

U.S. PATENT DOCUMENTS

| | | |
|---|---|---|
| 2,853,497 | 9/1958 | Holly et al. |
| 5,281,722 * | 1/1994 | Blaschke et al. ............ 549/39 |
| 5,463,093 * | 10/1995 | Garnett ............ 554/102 |
| 5,650,429 * | 7/1997 | Conrad et al. ............ 514/440 |
| 5,679,697 | 10/1997 | Garnett. |
| 5,776,973 * | 7/1998 | Garnett ............ 514/440 |
| 5,925,668 * | 7/1999 | Biewenga et al. ............ 514/440 |
| 5,962,509 * | 10/1999 | Ishii et al. ............ 514/440 |
| 5,990,152 * | 11/1999 | Hettche et al. ............ 514/440 |
| 6,013,663 * | 1/2000 | Fujita et al. ............ 514/440 |
| 6,046,228 * | 4/2000 | Rice et al. ............ 514/441 |

FOREIGN PATENT DOCUMENTS

| | | |
|---|---|---|
| 36 26 116 | 3/1988 | (DE). |
| 0378204 | 7/1990 | (EP). |
| 0618231 | 10/1994 | (EP). |
| 0785187 | 7/1997 | (EP). |
| 0947503 | 10/1999 | (EP). |
| 758897 | 10/1956 | (GB). |
| WO98/01440 | 1/1998 | (WO). |

OTHER PUBLICATIONS

SMITH, P., "The Chemistry of Open–Chain Organic Nitrogen Compounds", Functions Derived from Ammonia, Amines, Amides, Imines, Nitriles, Isocyanates, etc., W.A. Benjamin, Inc., vol. 1, pp. 167–168, 1965.

FIDLER, et al., "Characterization in vivo and in vivo of tumor cells selected for resistance to syngeneic lymphocytemidated toxicity". Cancer Res. 36: 3160–3165, 1976.

SIGEL et al., "Stability and Structure of Binary and Ternary Complexes of a Lipoate and Lipoate Derivatives with $Mn^{2+}$, $Cu^{2+}$, nad $Zn^{2+}$ in Solution", Archives of Biochemistry and Biophysics, vol. 187, No. 1, pp. 208–214, Apr. 15, 1978.

OKAWARA et al., "Synhesis of Polymers Containing Lipoic Acid Structure and Study of the Acyl Transfer Reaction", Israel Journal of Chemistry, vol. 17, pp. 264–268, Apr. 30, 1978.

JOHNSON et al., "Localization of mitochondria in living cells with rhodamine 123," Proceedings of the National Academy of Sciences, USA 77; pp. 990–994, 1980.

Chemical Abstracts, vol. 127, No. 9, 1982, Columbus Ohio, abstracts No. 259589e, KATAOKA, Hiroyuki, "Analysis of Lipoic Acid", p. 302, XP002131666, abstract and Methods Enzymol, vol. 279, No. I, 1997, pp. 166–176, RN 196189–89–6 Octanoic Acid, 6,8–Bis' (ETHOXYCARBONYL)THIO.

Chemical Abstracts, vol. 97, No. 20, 1982, Columbus Ohio, abstract No. 168725s, pp. 368; XP002131655, abstract & JP 82 123107 A (POLA) Jul. 31, 1982.

HAMPEL et al., "Activated Charcoal" Glossary of Chemical Terms, $2^{nd}$ Edition, pp. 24–25, Van Nostrand Reinhold, 1982.

Chemical Abstracts, vol. 104, No. 1, 1986, Columbus Ohio, abstract No. 161793s, V.M. GANDHI, "Lipoic Acid and Diabetes II", p. 41, XP002131667, abstract & J. Biosci, vol. 9, No. 1–2, pp. 117–127, 1985.

DVORAK, H.F., "Tumors: wounds that do not heal; Similarities between tumor stroma generation and wound healaing", New England Journal of Medicine 315: pp. 1650–1659, 1986.

GRANT & HACKH'S, "Chemistry Dictionary", $5^{th}$ Edition, McGraw–Hill Book Co., pp. 14,24,298,408, 1987.

HILL et al, "Clonal heterogeneity, experimental metastatic ability, and p21 expression in H–ras–transformed NIH 3T3 cells."J. National Cancer Institute80; pp. 484–490, 1988.

WHALEN, G.F., Solid tumors and wounds; transformed cells misunderstood as injured tissue? Lancet 136: pp. 1489–1492, 1990.

PATEL et al, "Molecular biology and biochemistry of pyruvate dehydrogenase complexes" FASEB Journal 4: pp. 3224–3233, 1990.

(List continued on next page.)

Primary Examiner—Deborah C. Lambkin

(57) ABSTRACT

This invention relates to the identification of a novel class of therapeutic agents which selectively target and kill tumor cells and certain other types of diseased cells, and to compositions comprising lipoic acid derivatives which poison the pyruvate dehydrogenase complex specifically in such cells. This invention also provides for methods of using therapeutically effective amounts of the lipoic acid derivatives for the treatment of cancer and other diseases. The lipoic acid derivatives described herein have a wide range of preventive and therapeutic applications.

27 Claims, 3 Drawing Sheets-

OTHER PUBLICATIONS

BAGGETTO, L.G., "Deviant energetic metabolism of glycoltic cancer cells", Biochemie 74: pp. 959–974, 1992.

Chemical Abstracts, vol. 117, No. 78, 1992, Columbus Ohio, abstract No. 39073k, F. BONOMI et al. "Synthesis and Characterisation of Metal Derivatives of Dihydrolipoic Acid" p. 889, XP002131664 abstract and Inorg. Chim, Acta, vol. 192, No. 2, pp. 237–242, Italy, 1992.

SUZUKI et al., "Antioxidant Activities of Dihyrolipoic Acid and its Structural Homologs", Free Radical Research Communications, vol. 18, Abstract 1993.

KATAOKA et al., "Analysis of Lipoic Acid in Biological Samples by Gaschromatography with Flame Photometic Detection", Journal of Chromatography–Biomedical Applications, vol. 615, Jun. 2, 1993, Abstract.

GARRETT et al., C.M. Biochemistry, New York, Saunders College Publishing, pp. 495–498, 603, 1995.

FUJIWARA et al., "Synthesis and Characterization of Selenolipolylated H–Protein of the Glycine Cleavage System", The Journal of Biological Chemistry, pp. 19880–19883, vol. 272, No. 32, Aug. 8, 1997.

NIEBCH et al., "Enantioselective high–performance liquid chromatography assay of (+)R–and (–)S–alpha–lipoc acid in human plasma", Chirality, vol. 9, Abstract 1997.

SEN et al., "A Positively Charged a–Lipoic Acid Analogue with Increased Cellular Uptake and More Potent and Immunomodulatory Activity", Biochemical and Biophysical Research Communications, vol. 247; pp. 223–228, Apr. 28, 1998.

STACPOOLE et al., "Pharamacokinetic, metabolism and toxicology of dichloroacetate", Drug Metabolism Reviews; 30: pp. 499–539, 1998.

DEAN, John A., "Nomenclature of Organic Compounds", Handbook of Organic Chemistry, McGraw–Hill Book Co., pp. 1-1 –1-5.

\* cited by examiner

Selective killing of diverse tumor cell types by bis-benzoyl lipoate

LIPOIC ACID DERIVATIVES AND THEIR USE IN TREATMENT OF DISEASE

This application claims priority to provisional patent application U.S. Ser. No. 60/105,628 filed Oct. 26, 1998.

FIELD OF THE INVENTION

The present invention relates to therapeutics and diagnostics for cancer and other diseases associated with altered metabolic enzymes. In particular, the invention relates to a novel class of therapeutic agents which selectively target and kill tumor cells, and certain other types of cells involved in disease processes.

BACKGROUND OF THE INVENTION

All mammalian cells require energy to live and grow. Cells obtain this energy by metabolizing food molecules. The vast majority of normal cells utilize a single metabolic pathway to metabolize their food. The first step in this metabolic pathway is the partial degradation of glucose molecules to pyruvate in a process known as glycolysis or glycolytic cycle. The pyruvate is further degraded in the mitochondrion by a process known as the tricarboxylic acid (TCA) cycle to water and carbon dioxide, which is then eliminated. The critical link between these two processes is a large multi-subunit enzyme complex known as the pyruvate dehydrogenase ("PDH") complex (hereinafter "PDC"). PDC functions as a catalyst which funnels the pyruvate from the glycolytic cycle to the TCA cycle.

Most cancers display profound perturbation of energy metabolism. This change in energy metabolism represents one of the most robust and well-documented correlates of malignant transformation.

Because tumor cells degrade glucose largely glycolytically, i.e., without the TCA cycle, large amounts of pyruvate must be disposed of in several alternate ways. One major pathway used for disposal of excess pyruvate involves the joining of two pyruvate molecules to form the neutral compound acetoin. This generation of acetoin is catalyzed by a tumor-specific form of PDC. Although the TCA cycle still functions in cancer cells, the tumor cell TCA cycle is a variant cycle which depends on glutamine as the primary energy source. Tumor-specific PDC plays a regulatory role in this variant TCA cycle. Thus, inhibition or inactivation of a single enzyme, namely tumor-specific PDC can block large scale generation of ATP and reducing potential in tumor cells.

In spite of the extensive work characterizing tumor cell metabolism, the systematic alteration of tumor cell energy metabolism has remained unexploited as a target for cancer chemotherapy. Many malignant diseases continue to present major challenges to clinical oncology. For example prostrate cancer is the second most common cause of cancer death in men. Current treatment protocols rely primarily on hormonal manipulations. However, in spite of initial high response rates, patients often develop hormone-refractory tumors, leading to rapid disease progression with poor prognosis. Overall, the results of cytotoxic chemotherapy have been disappointing, indicating a long felt need for new approaches to prevention and treatment of advanced cancers. Other diseases resulting from abnormal cell replication, for example metastatic melanomas, brain tumors of glial origin (e.g. astrocytomas), and lung adenocarcinoma, are also highly aggressive malignancies with poor prognosis. The incidence of melanoma and lung adenocarcinoma has been increasing significantly in recent years. Surgical treatments of brain tumors often fail to remove all tumor tissues, resulting in recurrences. Systemic chemotherapy is hindered by blood barriers. Therefore, there is an urgent need for new approaches to the treatment of human malignancies including advanced prostate cancer, melanoma, brain tumors, and other malignancies such as neuroblastomas, lymphomas and gliomas.

The development of the methods and compositions of the present invention was guided by the theory that metabolic traits distinguishing tumors from normal cells can lead to targets for therapeutic intervention. For instance, tumor cells appear to function metabolically through a tumor-specific PDC. Thus, inhibitors of this enzyme complex can be used to block tumor cell metabolism, thereby resulting in selective tumor cell death.

Anti-cancer activity has been proposed for certain palladium containing lipoate compounds, wherein the specific agent causing the anti-cancer effect was identified as the palladium. U.S. Pat. Nos. 5,463,093 and 5,679,679. Unlike the prior art, the present invention relates to a new class of lipoate compounds which do not contain palladium, yet surprisingly possess potent anti-cancer activity. These compounds are believed to function through PDC, and thereby provide an effective counter-measure against cancer and other pathological or pathogenic cells that show correspondingly altered energy metabolism.

Thus, it is a general object of the invention to provide a new class of therapeutic agents that effectively target and kill tumor cells.

It is another object of the invention to provide pharmaceutical compositions comprising lipoic acid derivatives and a pharmaceutically acceptable carrier capable of specifically targeting and killing tumor cells.

It is also an object of this invention to provide a method of prophylactic or therapeutic treatment for a variety of cancers using the lipoic acid derivatives described herein.

It is another object of this invention to provide prophylactic or therapeutic treatment of pathologies such as bacterial, fungal, plant and protozoan infections of humans and other animals using the lipoic acid derivatives described herein.

SUMMARY OF THE INVENTION

The present invention provides a novel class of compounds and their use in a method of treating various pathologies in a subject. The class of compounds comprise lipoic acid derivatives and pharmaceutically acceptable salts thereof. One preferred class of compounds comprise the structure of formula I:

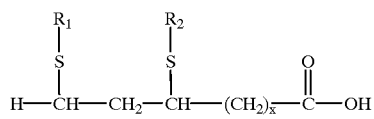

wherein:
x is 0–16
$R_1$ and $R_2$ are independently acyl $R_3C(O)$; wherein $R_3$ is an alkyl or aryl group; alkyl $C_nH_{2n+1}$; alkenyl $C_mH_{2m-1}$; alkynyl $C_mH_{2m-3}$; aryl, alkyl sulfide $CH_3(CH_2)_n$—S—; imidoyl $CH_3(CH_2)_nC(=NH)$—; and semiacetal $R_4CH(OH)$—S—; wherein $R_4$ is $CCl_3$ or COOH; and wherein n is 0–10 and m is 2–10.

Another preferred class of compounds comprise the structure of formula II:

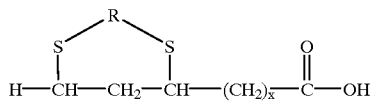

wherein:
x is 0–16; and
R is a non-palladium metal chelate.

One or both of the thiol portions of the lipoic acid composition may be altered or complexed (i.e., derivatized) with an additional reagent or moiety. The preferred lipoic acid derivative for treatment will vary according to the cell type and/or disease to be targeted.

The present invention also relates to a method of treatment of a mammal, including a human which is suffering from a condition, which method comprises administering to said mammal a therapeutically effective amount of at least one compound of formula I or II or a physiologically acceptable salt thereof.

Further provided is a method of treating or preventing a neoplastic condition in a subject comprising administering an effective amount of at least one compound of formula I or II or a physiologically acceptable salt thereof. This method encompasses a method where the compound is administered alone or in combination with another reagent. The combination treatment method provides for simultaneous, sequential or separate use in treating such conditions.

The treatment according to the invention, enables effective inhibition of tumor cells in a patient. Alternatively, the composition can be used to contact cells directly and inhibit or kill tumor cells in vitro. Moreover, other disease states may also exhibit sensitivity to the lipoic acid derivatives. Accordingly, the invention contemplates the use of lipoic acid derivatives as effective agents against diseases of eubacterial, archeal, fungal, plant, algal and protozoal origin as these diseases occur in humans and other animals.

The present invention also relates to a pharmaceutical composition which comprises a compound of formula I or II or a physiologically acceptable salt thereof together with one or more physiologically acceptable carriers or excipients.

DETAILED DESCRIPTION OF THE PREFERRED EMBODIMENTS

Structural Characteristics of Lipoic Acid Derivatives

Figure 1:
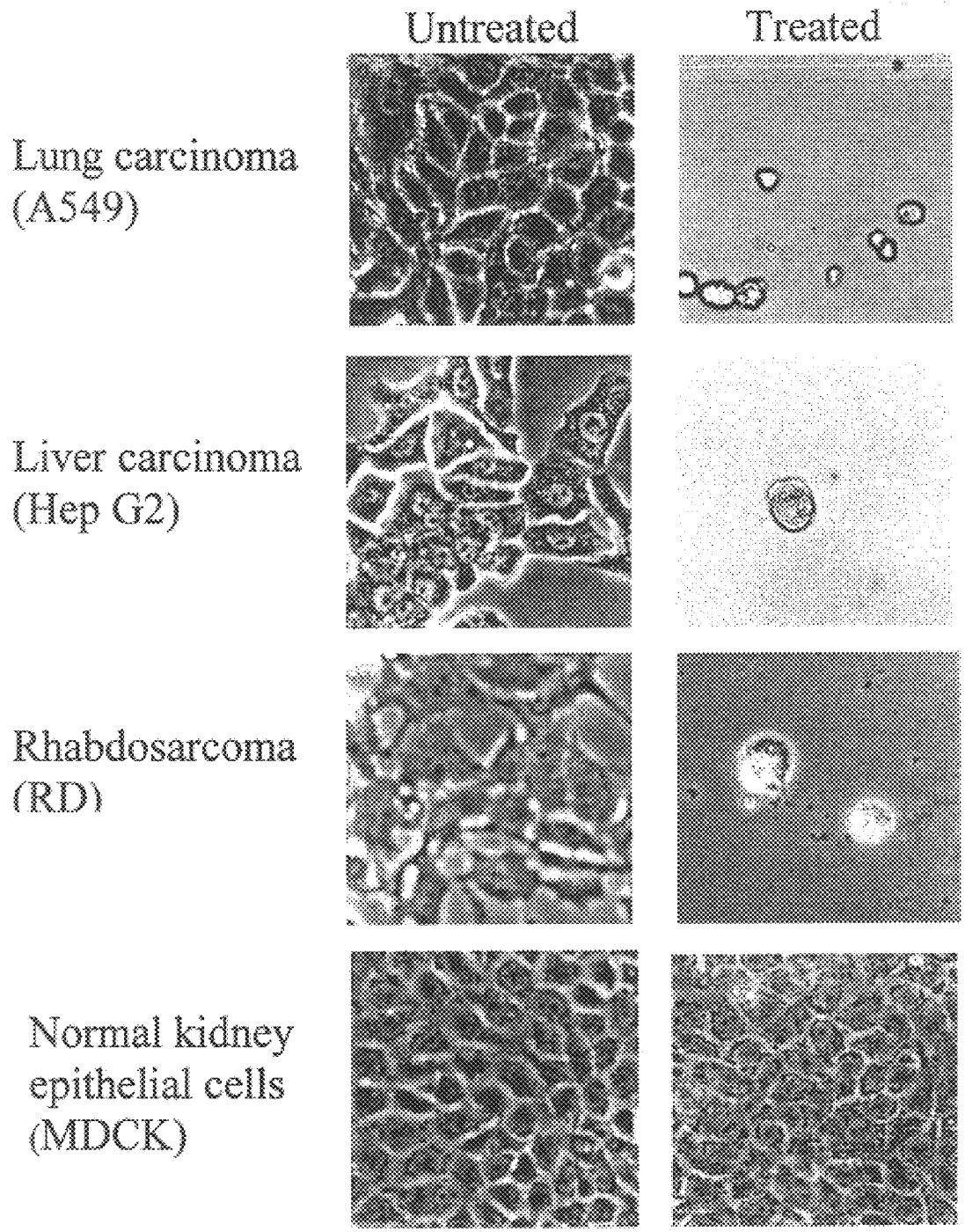
FIG. 1: Shown is cancer cell-specific cell killing by the bis-benzoyl lipoate (120 ug/ml or 120 mg/kg) member of the novel class of compounds that are the object of this invention. See EXAMPLE 9. The lefthand column contains the tissue of origin of the cancer and, in parenthesis, the specific cell line designation. The top three rows show three distinct cancer cell types—lung cancer, liver cancer and embryonic cancer. In contrast, the bottom row shows a normal (non-cancerous) kidney epithelial cell line. The central column shows the untreated (control) samples, while the rightmost column shows effects of treatment on each cell type (experimental samples). Note each of the three cancer cell types is efficiently killed, while the normal cells are not detectably affected. These images were photographed at ca. 48 hours after administration of the bis-benzoyl lipoate. Notice that almost all the cancer cells have been killed by this time. The few remaining cells or cell-fragments have morphology characteristic of cells undergoing cell death (apoptosis; see EXAMPLE 11; also see FIGS. 2 and 3). These few remaining cells in the treated fields will die within the next few hours. In contrast, note that the normal, noncancerous cells (bottom row) are not detectably effected by treatment.

The compounds of our invention embrace lipoic acid that has been derivatized on the thiol portion of the molecule by organic groups. Lipoic/dihydrolipoic acid species having shorter or longer carbon chains, up to 20 carbons in length, preferably between 4 to 10 carbon chain length, may be used to practice this invention. The variants of lipoic acid of the present invention include those in which the carboxylic acid group is undisturbed, and in which one or both thiols and/or sulfhydryls are blocked by derivatization, in order to specifically kill tumor cells, through interference with tumor cell-specific PDC functions.

The present invention relates to a class of lipoic acid compositions. One preferred class of such compositions comprises the formula:

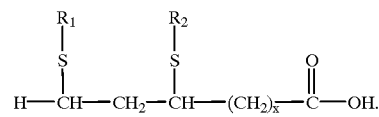

I

Wherein:
x is 0–16 and $R_1$ and $R_2$ can be independently:
(1) An acyl group linked through a thio-ester linkage. The acyl group preferably comprises RC(O)—; wherein R is alkyl or aryl group. Examples of acyl groups include but are not limited to acetyl and butaryl. A specific example of acyl derivatized lipoic acid is bis-acetyl lipoate (Example 2)
(2) An aromatic group linked through a thio-ester linkage. Examples of aromatic groups include but are not limited to benzoyl or a benzoyl derivatives. A specific example of benzoyl derivatized lipoic acid is bis-benzoyl lipoate (Example 3).
(3) An alkyl group linked through an thio-ether linkage. The alkyl group preferably comprises alkyl $C_nH_{2n}+1$ wherein n is 1–10. Such alkyl groups may be substituted with other moieties such as for example OH, Cl or $NH_2$. Examples of alkyl groups include but are not limited to methyl, ethyl, butyl, decanyl and 6,8-bis carbomoyl methylipoate. (EXAMPLE 5).
(4) An alkene group linked through an thio-ether linkage. The alkene may preferably comprise alkenyl $C_nH_{2n-1}$ wherein n is 2–10. Examples of alkene groups include but are not limited to propylene, 2,3 dimethyl-2-butene, and heptene.
(5) An alkyne group linked through a thio-ether linkage. The alkyne may preferably comprise $CnH_{2n-2}$ wherein n is 2–10. Examples of alkyne groups include but are not limited to acetylene, propyne and octyne.
(6) Alkyl, alkene and alkyne groups can be either open chains or alicyclics. Alicyclic groups may have additions or substitutions of any of the carbons to form heterocyclics. Examples of alicylic groups include but are not limited to cyclopropane, cyclopentene and 6,8 methyl-succinimido lipoate (EXAMPLE 6).
(7) Alkyl, alkene and alkyne groups can have additions on any of their carbons. Examples of additions include but are not limited to hydroxyls and amines.
(8) An aromatic or aryl group linked through an thio-ether linkage. The aromatic groups can be a benzene or a benzene derivative. Examples of benzene derivatives include but are not limited to toluene and aniline.
(9) Disulfide group alkyl sulfide $CH_3CH_n$—S—, where n can be but is not limited to 0–9) linked through a disulfide linkage.
(10) Imidoyl group $CH_3(CH_2)_nC(=NH)$— where n can be, but is not limited to 1–10] linked through a thio-amide linkage; and
(11) Semiacetal group RCH(OH)—S— where R is limited to compounds with strongly electron withdrawing substituents. Examples include trichloroacetaldehyde and pyruvic acid.

$R_1$ and $R_2$ may also comprise thio-esters that can be oxidized to produce sulfoxides or sulfones, for example, C—S(O)—R and C—S(O)$_2$—R respectively. $R_1$ and $R_2$ may further comprise disulfides that can be oxidized to thiosulfinic or thiosulfonic acids, for example C—S(O)—S—R and C—S(O)$_2$—S—R respectively A second class of lipoic acid compositions comprises the formula:

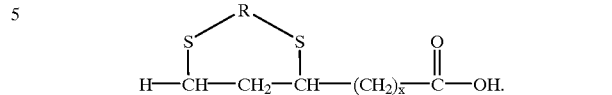

II wherein:
x is 0–16; and
R is a covalent bond, a metal chelate or other metal complex wherein said metal is not palladium.

In one preferred embodiment, the lipoic acid of the present invention is derivatized by addition of a blocking group(s) to one or both sulfhydryls. These blocking groups can take any form, such as aliphatic or aromatic organic substituents added to one or both sulfhydryls. The general structure of this class of lipoate derivatives is shown above. One specific example is as follows:

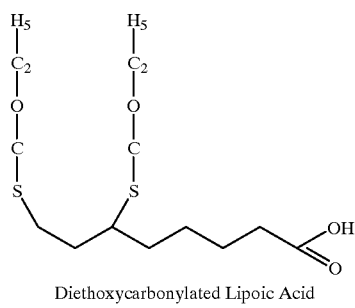

Diethoxycarbonylated Lipoic Acid

The compounds of our invention embrace lipoic acid that has been derivatized on the thiol portion of the molecule by organic groups.

Compounds are available which react specifically with thiol groups and are readily known in the art. Examples of such thiol specific reagents include N-ethylmalemide (NEM), 5,5-dithiobis (2-nitrobenzoic acid)(DNTB), p-chloromercuribenzoic acid (PCMB) and ethylchloroformate (ECF). In general, thiol reactive reagents form thioethers or thioesters with the reacting thiol(s), and all such compounds are members of this class.

Yet other derivatives of lipoic acid for practicing the invention are those in which one or both of the thiols have been replaced with a selenium molecule, a sulfur analog, or an analog in which one or both lipoic acid thiols are oxidized to sulfate or related groups.

In another embodiment, a metal or metal salt is added to one or both sulfhydryls through a bond in which a metal or metal salt forms a covalent, or coordination or chelated complex with the thiol group(s) of the lipoic acid molecule. Such metals include, platinum, nickel, silver, rhodium, cadmium, gold or cobalt. Metal salts include, for example, platinum bromide, platinum chloride, platinum iodide, nickel borate, nickel boride, nickel bromide, nickel chloride, nickel iodide, nickel fluoride, silver bromate, silver bromide, silver chloride, silver fluoride, silver iodide, rhodium chloride, cadmium bromide, cadmium chloride, cadmium fluoride, cadmium iodide, gold bromide, gold chloride, gold iodide, cobalt bromide, cobalt bromide, cobalt chloride, cobalt fluoride, cobalt iodide. Such salts include various metal oxidation states such as, for example, platinum (II) chloride and platinum (IV) chloride. In general, the structure of the lipoic acid-metal complex described herein is likely to be (metal)$_m$ (lipoic acid)$_n$ where m and n are both one or (metal)$_m$ (lipoic acid)$_n$ wherein m is one and n is two.

Compositions of Lipoic Acid Derivatives for Therapeutic Use

For therapeutic applications, a pharmaceutical compositions comprising an effective amount of the lipoic acid derivatives described above along with pharmaceutically acceptable carrier is administered directly to a patient. The compositions may be in the form of tablets, capsules, powders, granules, lozenges, suppositories, reconstitutable powders, or liquid preparations such as oral or sterile parenteral solutions or suspensions. However, for consistency of administration it is preferred that the lipoic acid derivative composition be in the form of unit dose. For oral administration, tablets and capsules may contain conventional excipients, such as binding agents, tabletting lubricants, or pharmaceutically acceptable wetting agents such as sodium lauryl sulphate.

Solid oral compositions may be prepared by conventional methods of blending, filling, tabletting or the like. Repeated blending operations may be used to distribute the lipoic acid derivative throughout any compositions employing fillers. Such operations are, of course, conventional in the art. See for example *Remington's Pharmaceutical Sciences*, 17$^{th}$ Edition 1985, Gennaro ed., Mack Pub. Co., Pennsylvania, USA. The tablets may be coated according to methods well known in normal pharmaceutical practice, in particular with enteric coating. Oral liquid preparations may be in the form of, for example, emulsions, syrups, or elixirs, or may be presented as a frozen product for reconstitution with water or other suitable vehicle before use. Such liquid preparations may contain conventional additives such as suspending agents, emulsifying agents, non-aqueous vehicles (which may include edible oils), and if desired, conventional flavoring or coloring agents.

For parenteral administration, fluid unit dosage forms are prepared utilizing the lipoic acid derivative and a sterile vehicle, and, depending on the concentration used, can either be suspended or dissolved in the vehicle. In preparing solutions, the lipoic acid derivative can be dissolved in water for injection and filter sterilized before filling into a suitable vial or ampoule and sealing. Also, adjuvants such as local anaesthetic, a preservative, and buffering agents can be dissolved in the vehicle. To enhance stability, the composition can be frozen after filling into the vial and the water removed under vacuum. Parenteral suspensions are prepared in substantially the same manner, except that the lipoic acid derivative is suspended in the sterile vehicle. A surfactant or wetting agent can be included in the composition to facilitate uniform distribution of the lipoic acid derivative.

In the methods of preventing or inhibiting cancer, the lipoic acid derivative, or a pharmaceutical composition comprising a lipoic acid derivative, may be administered via one of several routes including intravenous, intramuscular, subcutaneous, intradermally, intraperitoneal, intrathoracic, intrapleural, intrauterine, topical, or intratumor.

Those skilled in the art will recognize that the mode of administering the lipoic acid derivative depends on the type of cancer, or symptom to be treated. For example, a preferred mode of administering the lipoic acid for treatment of leukemia would involve intravenous administration, whereas preferred methods for treating skin cancer would involve, for example, topical or intradermal administration.

The pharmaceutical compositions of the invention may contain from 0.1% to 99% by weight, preferably from 10% to 25% by weight of the lipoic acid derivative, depending on the method of administration.

Methods for Using Lipoic Acid Derivatives

The lipoic acid derivatives of the invention may be used in a method for preventing or inhibiting diseases involving altered or distinct cellular PDC activity. Such diseases are characterized by a sensitivity to the lipoate compositions of the present invention. One of the most important advantages of our lipoic acid derivatives as chemotherapeutic agents is their specificity. Cells with appropriately altered or deranged energy metabolism, i.e. altered PDC activity, are particularly targeted and killed, while surrounding healthy tissues remain unharmed by the lipoic acid reagent. The skilled artisan can readily identify diseases having altered PDC activity. Alternatively the skilled artisan can readily screen their disease of interest for its sensitivity to the instant class of compounds.

In a preferred treatment method, the instant lipoic acid compositions are used for the prevention and treatment of cancers such as primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer, colon cancer, and adenocarcinomas such as breast cancer, prostate cancer, ovarian cancer, pancreatic cancer. A wide variety of tumor types, including cervical carcinomas and breast cancers, are sensitive to this new class of compounds. Cellular results showing cancer-specific cell killing can be seen, for example in Table 1, herein below.

The preferred dosage of the lipoic acid derivative, or pharmaceutical composition thereof, is selected based on other criteria, including the particular composition employed and the age, weight, and condition of the individual. Importantly, the quantity of lipoic acid derivative used should be sufficient to inhibit or kill tumor cells while leaving normal cells substantially unharmed. In general, it is desirable to provide the patient with a dosage of lipoic acid derivative of at least about 10 $\mu$M, preferably at least about 100 $\mu$M, more preferably at least about 400 $\mu$M, while a range of from about 10 $\mu$M to about 1 mM is contemplated, of course, a lower or higher dose may be administered, guided by the in vivo data set forth in the Examples described herein. As stated above, a variety of clinical factors will influence the preferred dosage ranges.

Another embodiment of the invention relates to a method of treating a disease sensitive to lipoate derivatives comprising administering an effective amount of a lipoate compound and a second reagent to treat said disease. This second reagent is preferably an inhibitor of mitochondrial energy metabolism and/or one that induces apoptosis. Such reagents include metabolism inhibitory reagents. Many such reagents are known in the art. One particularly preferred reagent is dichloroacetate. This second reagent may be administered sequentially, simultaneously or separately, so as to amplify patient response to said treatment method.

By adapting the treatments described herein, the lipoic acid derivatives may also be used in methods for treating diseases other than cancer, where the disease-causing cells exhibit altered metabolic patterns. For example, eukaryotic pathogens of humans and other animals are generally much more difficult to treat than bacterial pathogens because eukaryotic cells are so much more similar to animal cells than are bacterial cells. Such eukaryotic pathogens include protozoans such as those causing malaria as well as fungal and algal pathogens. Because of the remarkable lack of toxicity of the lipoic acid derivatives of the invention to normal human and animal cells and because many eukaryotic pathogens are likely to pass through life cycle stages in which their PDC's become sensitive to members of the novel class of lipoate derivates described here, some members of the novel class of lipoate derivatives described herein kill bacterial PDC's and thus represent a fundamentally new class of antibacterial agents. As bacteria resistant to traditional antibiotics are becoming an increasingly severe clinical problem, these compounds will prove to be of therapeutic importance in this context.

In yet other applications, the lipoic acid derivatives of the present invention are used as diagnostic agents in vitro. As stated earlier, depending on the specific tumor cell or cell type in question, different lipoic acid derivatives may be more or less effective at inhibiting distinct tumor classes. Thus, for example, in cases where diagnosis or selection of an appropriate chemotherapeutic strategy may be difficult, testing of a culture of tumor cells in vitro with lipoic acid derivatives known to target specific tumor cell types provides an alternative approach for identifying tumor types and effective treatments.

EXAMPLES

Example 1

The synthetic conditions allowing the production of a metal/lipoate derivative is described here as follows:

$PtCl_2$ was obtained from Alfa Aesar, DL-alpha lipoic acid from USB, all other chemicals from Fisher. The formulation given produces a final volume of 1 mL of the platinum/lipoate derivative solutuion.

1. Suspend 10.64 mg $PtCl_2$ in 215 ul of 3.5N HCL.
2. Heat for 15 minutes at 65° C.
3. Centrifuge for 6 minutes at room temperature at 10,000×g and recover cleared supernatant.
4. Dissolve 114 mg of NaOH in 1.5ml of $H_2O$.
5. Add 82 mg of DL-alpha lipoic acid to the NaOH solution from step 4 and dissolve.
6. Transfer 150 ul of the Sodium lipoate solution from step 5 into a fresh tube and add 22 ul of the cleared platinum chloride supernatant from step 3.
7. Mix until all precipitate dissolves.
8. Heat at 65° C. for 15 minutes.
9. Bring to final volume of 1 ml with distilled $H_2O$.

Example 2

In order to confirm the existence of a large, new class of anti-cancer agents consisting of blocked and/or disabled lipoic acid derivatives, a number of new lipoic acid derivatives have been synthesized and tested. In this and the following five EXAMPLES (2–7), the synthesis, structure and purification of six compounds are described. These compounds are then tested in later EXAMPLES (8–15).
Preparation of 6,8-Bisacetylmercaptooctanoic Acid (Bis-acetyl Lipoic Acid)

6,8-bisacetylmercaptooctanoic (henceforth referred to as bis-acetyl lipoic acid) was prepared from commercially available -lipoic acid using a three step procedure. These steps were as follows: Lipoic acid was first reduced to 6,8-bismercaptooctanoic acid which was then acetylated to produce 6,8-bisacetylmercaptooctanoic acetic anhydride. This 6,8-bisacetylmercaptooctanoic acetic anhydride was then selectively hydrolyzed to produce the 6,8-bisacetylmercaptooctanoic acid.

In detail these steps were accomplished as follows.
Step 1
6,8-Bismercaptooctanoic Acid A-Lipoic acid (5.15 g, 25.0 mmol) was suspended in 125 mL of water and sodium bicarbonate (2.10 g, 25.0 mmol) added. The mixture was sonicated to generate the sodium salt. The resulting pale yellow solution was cooled in an ice bath and solid sodium borohydride (1.90 g, 50.0 mmol) added with stirring in small portions over 20 min. The solution was stirred at ice bath temperature another 30 min, and then at room temperature for 30 min. The cloudy solution was cooled in an ice bath, and the pH brought to about 1 by the slow addition of 2M hydrochloric acid. A vigorous evolution of hydrogen occurred as the excess sodium borohydride decomposed and an oily liquid separated. As much as possible the following operations were performed under nitrogen. The mixture was extracted with 3×50 mL of chloroform. The combined chloroform extracts were dried over magnesium sulfate, filtered and the solvent evaporated under reduced pressure at room temperature. The oil remaining was further dried under vacuum to remove the last traces of solvent. The 6,8-bismercaptooctanoic acid was isolated as a colorless oil weighing 5.2 g (100% yield). The product was stored at −20° under nitrogen.

Analysis produced the following results: 1H-NMR ($CDCl_3$): 2.89 (multiplet, 1H, S—C—H). 2.67 (multiplet, 2H, S—CH2), 2.34 (t, J=7.1 Hz, 2H, CH2C(O)), 1.4–1.92 (multiplets, 8H, (CH2)2), 1.33 (t, J=8.0 Hz, 1H, S—H), 1.30 (t, J=7.6 Hz, 1H, S—H).

13C-NMR ($CDCl_3$): 180.0, 42.7, 39.2, 38.6, 33.8, 26.4, 24.2, 22.2

Step 2
6,8-Bisacetylinercaptooctanoic Acetic Anhydride 6,8-bismercaptooctanoic acid (5.20 g, 25 mmol) was dissolved in 125 mL of dry methylene chloride under nitrogen and triethylamine (8.10 g, 80.0 mmol, 11.25 mL) was added. The solution was cooled in an ice bath and acetyl chloride (6.30 g, 80.0 mmol) dissolved in 25 mL of methylene chloride added dropwise with stirring over 15 min. Triethyl ammonium chloride precipitated during the addition. The solution itself remained colorless. Stirring was continued at room temperature for 90 min. The volume was brought to 300 mL with more methylene chloride (all the solid dissolved) and the solution transferred to a separatory funnel. It was extracted quickly with 300 mL of 10% citric acid (the pH of the aqueous phase was checked after the extraction to be sure it was acidic). It was extracted a second time with 200 mL of the citric acid solution, and then washed with 200 mL of half saturated brine. The organic phase was dried over magnesium sulfate, filtered, and the methylene chloride evaporated. An almost colorless oil weighing 8.0 g remained.

Analysis produced the following results: 1H-NMR ($CDCl_3$): 3.49 (multiplet, 1H), 2.7–3.0 (multiplet, 2H), 2.36 (t, 2H, CH2C(O), 2.27 (s, 3H, CH3), 2.26 (s, 3H, CH3), 2.15 (s, 3H, CH3), 1.3–1.9 (multiplet, 8H).

$^{13}$CNMR ($CDCl_3$): 195.4, 195.2, 168.9, 166.3, 43.2, 34.8, 34.5, 34.2, 30.6, 30.4, 26.3, 25.7, 23.7, 22.0. IR (KBr pellet): 1821, 1749, 1691 cm−1.

Step 3
6,8-Bisacetylmercaptooctanoic Acid

The anhydride from step 2 (8.0 g) was mixed with 30 mL of water and 30 mL of 2-propanol and stirred at 40 for 4.25 hr. After about 2 hr there was a clear solution. The solvent was evaporated under vacuum (2 mm) at 25. The oil remaining was evaporated with 10 mL of water to remove any residual 2-propanol and acetic acid. An almost colorless oil weighing 6.8 g was isolated.
Purification An example purification is as follows. The material from step 3 was mixed with 5 mL of ethyl acetate-hexane-acetic acid (100:100:1, v/v) added to make it more fluid. The solution was applied to a 25×6.5 cm column of Silica Gel 60 (about 300 g of flash. silica) packed in ethyl acetate—hexane—acetic acid (100:100:1, v/v). The column was eluted with this solvent. Fractions of 75 mL were collected at about 5 mL/min. About a 1:1 mixture of the product and a slightly faster eluting impurity was collected in fraction 13 (0.86 g). Fractions 14 (1.92 g) and 15 (1.61 g) contained the product with much less of this impurity. Pure material was collected in fractions 16–20 (2.36 g) as a colorless oil. Fractions 14 and 15 were rechromatographed (separately) on a 25×4.5 cm column (150 g of Silica gel). Isolated 1.72 and 1.55 g of pure product respectively. Overall yield of pure product was 5.63 g (77% yield based on 6,8-bismercaptooctanoic acid).

Analysis produced the following results: $^1$H-NMR (CDCl$_3$): 3.50 (multiplet, 1H), 2.7–3.0 (multiplet, 2H), 2.27 (t. 2H, CH$_2$C(O)), 2.27 (s, 3H, CH3), 2.26 (s, 3H, CH$_3$), 1.1–1.8 (multiplet, 8H).

$^{13}$C-NMR (CDCl$_3$): 195.67, 195.50, 179.59, 43.34, 34.60, 34.30, 33.71, 30.68, 30.48, 26.40, 26.01, 24.20.

IR(neat liquid): 2935,1736,1691,1423,1355, 1134, 1118, 953, 744, 630.

TLC R$_f$=0.40 (ethyl acetate-hexane-acetic acid, 100:100:1, v/v).

Purity

Analysis indicates that the final product of this synthesis (bis-acetyl lipoic acid) has greater than 98% purity. Moreover, five independent batches were produced in the course of these studies and the biological properties (summarized in EXAMPLE 8) of all batches were indistinguishable in every tested detail. The structure of this compound is illustrated below.

Example 3

Preparation of 6,8-Bisbenzoylmercaptooctanoic Acid (Bisbenzoyl Lipoic acid)

In overview, 6,8-Bisbenzoylmercaptooctanoic acid was prepared by a three step procedure from commercially available a-lipoic acid. The lipoic acid was first reduced to 6,8-bismercaptooctanoic acid with sodium borohydride in water under slightly alkaline conditions. The product was benzoylated with three equivalents of benzoyl chloride in the presence of triethylamine to scavenge the HCl byproduct to produce 6,8-bisbenzoylmercaptooctanoic benzoic anhydride. The anhydride was selectively hydrolyzed with dioxane/water to produce 6,8-bisbenzoylmercaptooctanoic acid without any undesired hydrolysis of the benzoylthio ester groups. The product was purified by column chromatography on Silica Gel. The purified acid was dissolved in methanol and converted to the sodium salt by the slow addition of an aqueous solution containing one mole equivalent of sodium bicarbonate.

In detail these step were carried out illustrated by the following example:

Step 1

6,8-bismercaptooctanoic acid was prepared exactly as described in EXAMPLE 2.

Step 2

6,8-Bisbenzoylmercaptooctanoic Benzoic Anhydride 6,8-bismercaptooctanoic acid (2.03 g, 10 mmol) was dissolved in 50 mL of dry methylene chloride under nitrogen and triethylamine (3.24 g g, 32 mmol, 4.50 mL) was added. Benzoyl chloride (4.50 g, 32 mmol) dissolved in 20 mL of methylene chloride was added dropwise with stirring over 20 min. Triethyl ammonium chloride precipitated when about half the benzoyl chloride was added. The solution itself remained colorless. Stirring was continued at 25–270 for 9 hr. The volume was brought to 100 mL with more methylene chloride (all the solid dissolved) and the solution transferred to a separatory funnel. It was extracted quickly with 2×50 ml of 10% citric acid (the pH of the aqueous phase was checked after the extraction to be sure it was acidic), and then washed with 50 mL of saturated brine. The organic phase was dried over magnesium sulfate, filtered, and the methylene chloride evaporated. An almost colorless oil weighing 5.48 g remained.

Step 3

6,8-Bisbenzoylmercaptooctanoic Acid

The crude anhydride (5.48 g) was dissolved in 20 mL of dioxane and 20 mL of water was added. This caused material to oil out. The mixture was stirred at 40–450 for 21 hr. The solvent was evaporated under vacuum (2 mm) at 30°. The oil remaining was taken up in 80 mL of chloroform and extracted with 25 mL of 5% aqueous citric acid. The organic phase was dried over magnesium sulfate, filtered, and the solvent evaporated. A faintly yellow oil weighing 5.7 g was isolated. NMR spectra showed that only about one third of the anhydride had been hydrolyzed. Therefore, crude material was redissolved in 20 mL of dioxane and 10 mL of water added. The mixture was stirred at 450 a further 32 hr. The solvent was evaporated in vacuo. After this treatment, the hydrolysis of the anhydride was complete.

Purification

The product was mixed with 2 mL of ethyl acetate and applied to a 25×4.5 cm column of Silica Gel 60 (150 g of flash silica) packed in hexane-ethyl acetate-acetic acid (100:50:1, v/v). The column was eluted with this solvent. Fractions of 40 mL were collected at about 5 mL/min. Faster eluting material was collected in fractions 10–12 (1.33 g of a white solid—probably benzoic acid). A small amount of this faster eluting material along with the product the product was collected in fractions 13–15 (0.66 g). Pure product was collected in fractions 16–21 (1.95 g of a colorless oil).

Analysis produced the following results: 1H-NMR (CDCl3): 8.0 (multiplet, 4H, ArH), 7.38–7.60 (multiplet, 6H, ArH), 3.89 (multiplet, 1H, CH—S), 3.0–3.3 (multiplet, 2H, CH2S), 2.34 (t, J=7.1 Hz, 2H, CH2C(O)), 1.1–2.2 (multiplet, 8H, —CH2—).

13C-NMR (CDCl3): 191.71, 191.46, 179.72, 136.98, 136.92, 133.29, 128.51, 127.25, 127.14, 43.60, 34.98, 34.59, 33.76, 26.43, 26.19, 24.29.

TLC Rf=0.30 (hexane-ethyl acetate-acetic acid, 100:50:1, v/v).

IR (neat liquid): 2937, 1710, 1704., 1662, 1667, 1655, 1448, 1207, 1175, 911, 773, 757, 733, 648, 688 cm−1.

Sodium Salt

The sodium salt of this derivative is more soluble and easier to work with. It therefore is generally preferred to produced the material in the salt form as illustrated by the following example. The acid (1.95 g, 4.7 mmol) was dissolved in 10 mL of methanol, and a solution of sodium bicarbonate (0.39 g, 4.7 mmol) in 10 mL of water was added in small portions with vigorously swirling over about 10 min. At first material oiled out but when addition was complete there was a colorless homogeneous solution. The solution was left at room temperature another 10 min then the solvent was removed under vacuum (2 mm) at 20 leaving a gummy solid. The solid was dissolved in 10 mL of methanol and the solvent flashed off in vacuo. This was repeated a second time. A foamy white solid was produced. This was dried in vacuo over P2O5 at room temperature overnight. Isolated 1.60 g of the salt.

Analysis produced the following results: 1H-NMR (D2O): 7.8–7.9 (multiplet, 4H, ArH), 7.0–7.4 (multiplet, 6H, ArH), 3.57 (multiplet, 1H, —CH—S), 2.9–3.1 (multiplet, 2H, CH2S), 2.06 (t, 2H, CH2C(O)), 1.0–2.1 (multiplet, 8H, —CH2—).

13C-NMR (D2O): 193.49, 193.11, 183.39, 137.10, 137.00, 134.21, 129.21, 127.70, 127.58, 44.69, 38.15, 34.97, 27.23, 27.00, 26.46.

Purity

Analysis indicated that the preparations of bis-benzoyl lipoate were greater than 98% pure. Moreover, each of three independent preparations of this agent showed indistinguishable biological properties (see EXAMPLE 8).

The structure of this compound is illustrated below.

Example 4

Preparation of 8-Acetylmercapto-6-mercaptooctanoic Acid (Monoacetyl Lipoate)

8-Acetylmercapto-6-mercaptooctanoic Acid

Acetyl chloride (0.30 g, 3.8 mmol) in 4 mL of dry methylene chloride was added dropwise under a nitrogen atmosphere over 10 min to a stirred solution of 6,8-bismercaptooctanoic acid (0.80 g, 3.8 mmol) and triethylamine (1.16 g, 11.5 mmol) at 0. The solution was stirred at 0 a further 15 min then at room temperature for 2 hr. The solution was diluted to 75 mL with methylene chloride and extracted with 2×50 mL of 10% aqueous citric acid, then washed with 30 mL of saturated brine. The organic phase was dried (MgSO4), filtered and the solvent evaporated. The oil remaining was dissolved in 8 mL of 2-propanol and 8 mL of water added. The mixture was stirred under nitrogen at 40 for 4.5 hr. The solvent was evaporated in vacuo and the crude product mixture separated by column chromatography on silica gel first using ethyl acetate-hexane-acetic acid (100:100:1, v/v) as the eluting solvent, and then rechromatographed using hexane-ethyl acetate-acetic acid (150:100:1, v/v) as the solvent yielding 51 mg (5%) of pure 8-acetylmercapto-6-mercaptooctanoic acid as a colorless oil.

Analysis produced the following results: 1H-NMR (CDCl3): 3.0 (m, 2H, —CH2S), 2.78 (m, 1H, —CHS—), 2.34 (t, J=7.1 Hz, 2H, —CH2COOH), 2.30 (s, 3H, CH3C(O)), 1.4–2.0 (m, 8H, —CH2—), 1.35 (d, J=7.6 Hz, 1H, SH).

13C-NMR (CDCl$_3$): 195.79, 179.77, 39.79, 38.60, 38.41, 33.81, 30.56, 26.78, 26.34, 24.19.

IR (neat): 2935, 1707, 1692, 1414, 1354, 1283, 1257, 1232, 1135, 952, 628.

TLC Rf=0.41; Silica gel G: hexane-ethyl acetate-acetic acid, 150:100:1, (v/v).

Example 5

Preparation of 6.8-Biscarbamoylmethylmercaptooctanoic Acid 6,8-Biscarbamoylmethylmercaptooctanoic Acid Iodoacetamide (1.11 g, 6.0 mmol) was added to a solution of 6,8-bismercaptooctanoic acid (0.62 g, 3.0 mmol) dissolved in 30 mL of degassed methanol-water (9:1, v/v) at 0. The solution was stirred under nitrogen under subdued light and 1.0 M aqueous sodium hydroxide (9.0 mL, 9.0 mmol) added over 3 min. The clear solution was stirred at 0 for 10 min and then at room temperature for 4 hr. The bulk of the methanol was evaporated under reduced pressure and the volume brought to 25 mL with degassed water. The pH was adjusted to 1 with 2 M hydrochloric acid. The water was evaporated in vacuo at 25, and the light yellow oil remaining shaken with 2×20 mL of ethyl acetate. The ethyl acetate insoluble material was chromatographed on silica gel using chloroform-methanol-acetic acid (120:60:1, v/v) as the eluent affording 1.0 g (100%) of the 6,8-biscarbamoylmethyl-mercaptooctanoic acid as a brownish-yellow solid.

Analysis produced the following results: 1H-NMR (D2O): 3.44 (s, 2H, —CH2C(O)NH2), 3.43 (s, 2H, —CH2C(O)NH2), 3.00 (m, 1H, —CHS), 2.88 (t, J=7.4 Hz, 2H, CH2S), 2.51 (t, J=7.1 Hz, 2H, —CH2COOH), 1.95 (m, 2H, —CH2—), 1.5–1.8 (m, 6H, —CH2—).

13C-NMR (D2O): 180.07, 175.51, 175.24, 46.00, 35.65, 35.09, 34.11, 34.09, 34.03, 30.29, 26.29, 25.13.

TLC Rf=0.35; Silica gel G: chloroform, methanol acetic acid, 60:30:1, (v/v).

Example 6

Preparation of 6,8-Bis-[S-(N-methylsuccinimido)] mercaptooctanoic Acid 6,8-Bis-[S-(N-Methylsuccinimido)]Mercaptooctanoic Acid 6,8-Bismercaptoocatanoic acid (0.62 g, 3.0 mmol) was mixed with sodium bicarbonate (0.25 g, 3.0 mmol) dissolved in 25 mL of degassed water and stirred under nitrogen at room temperature until a clear solution was produced. N-Methylmaleimide (0.67 g, 6.0 mmol) was added and the mixture stirred at room temperature under nitrogen for 3 hr. The solution was filtered to remove a trace of insoluble material then washed with 20 mL of chloroform. The pH of the aqueous phase was adjusted to 1.5 with 2 M hydrochloric acid and the mixture extracted with 3×15 mL of chloroform. The chloroform extracts were dried (MgSO4), filtered and the solvent evaporated leaving a colorless syrup weighing 1.30 g. The TLC [Silica gel, (chloroform-methanol, 10:1, (v/v)] showed a number of overlapping spots with Rf=0.27 as expected for the mixture of diastereomers which is possible.

Analysis produced the following results: 1H-NMR (CDCl3): 3.72 (m, 2H), 2.7–3.3 (m, 5H), 2.93 (s, 6H, CH3—), 2.25–2.55 (m, 4H), 2.0–1.35 (m, 8H).

13C-NMR (CDCl3): 178.73, 176.81, 176.77, 176.65, 176.62, 176.54, 176.50, 174.75, 174.69, 45.22, 44.78, 44.57, 39.11, 38.96, 38.90, 38.77, 38.59, 38.51, 38.00, 37.68, 36.35, 36.30, 36.24, 35.87, 35.85, 35.78, 34.49, 34.34, 33.96, 33.79, 33.67, 33.52, 29.08, 28.70, 28.66, 28.45, 25.92, 25.86, 25.58, 25.45, 25.02, 24.98, 24.21, 24.14.

Example 7

Preparation of Sodium 6.8-Dihydroxyoctanoate

Sodium 6,8-Dihydroxyoctanoate

Methyl 6,8-dihydroxyoctanoate (0.15 g, 0.80 mmol; containing about 10% of the 6,7-isomer) was dissolved in 3 mL of methanol and 1.00 M sodium hydroxide in methanol (0.80 mL, 0.80 mmol) was added. The solution was stirred under reflux for 3 hr. The solvent was evaporated in vacuo yielding 0.15 g of sodium 6,8-dihydroxyoctanoate as a white powder. Yield was quantitative.

Analysis produced the following results: 1H-NMR (D2O): 3.74 (m, 1H, —CHOH—), 3.70 (t, J=6.6 Hz, 2H, —CH2OH), 2.19 (t, J=7.2 Hz, 2H, —CH2COOH), 1.2–1.9 (m, 8H, —CH2—).

13C-NMR (D2O): 184.47, 69.25, 59.42, 39.01, 38.21, 36.77, 26.47, 25.32.

Example 8

EXAMPLES 9–12 describe results from cultured cell systems demonstrating the properties and efficacy of the lipoic acid derivative compounds that are the object of this invention. Table 1 below summarizes all the results found in EXAMPLES 9–12 in abbreviated and tabular form.

In overview, all of the Examples using the lipoic acid derivatives on tissue culture cells showed that the lipoic acid derivatives had the capacity to kill tumor cells, while leaving contact-inhibited, normal, noncancerous cells unharmed in the appropriate dose ranges.

Second, every cancer cell type tested was killed by one or more members of the family of blocked lipoic acid derivatives. This indicated that these agents have a broad range of potential clinical applications, including many or most human cancers.

Third, different lipoic acid derivative compounds had somewhat different chemical characteristics including, for example, solubility in polar and nonpolar environments, with corresponding effects on how efficiently different derivatives crossed the cell membrane and entered the cell. Moreover, the lipoic acid derivatives had different rates of utilization by the cellular enzymes that normally manage lipoic acid itself. Given these properties, it was observed that the different lipoic acid derivatives had somewhat different anti-cancer potencies. Some derivative had very high potencies, while others had lower, but still potentially useful, potencies.

Fourth, because different tumor cells types had different physiological properties, these properties could exert indirect effects both on the uptake and incorporation of lipoic acid derivatives, and on the toxic effects of this incorporation. Thus, it was discovered that different cancer cell types showed significantly different levels of sensitivity. The sensitivity of the different cancer cells ranged from relatively sensitive cancer cell types that were killed by all tested lipoic acid derivatives, through relatively resistant cancer cell types that were only efficiently killed by more potent lipoic acid derivative compounds.

In spite of these differences in potency, it is important to note that the lipoic acid derivatives share common properties described in the EXAMPLES below.

killed by treatment while "−" indicates that they were not. "±" indicates a slow marginal response seen only in a few special cases with fibroblasts experimentally transformed by introduction of the ras oncogene (EXAMPLE 10).

Example 9

This Example provides evidence that the lipoic acid derivatives of this invention kill cancer cells with high specificity. More specifically, the use of lipoic acid derivatives in cultured cell systems is described. The results show that the lipoate derivatives killed cancer (transformed) cells efficiently under conditions where noncancerous normal (non-transformed) cells were apparently unaffected. The data summarized in TABLE 1 in EXAMPLE 8 were generated using the following procedure:

First, each cell type to be tested was plated at low densities in the wells of a standard 6×24 well tissue culture plate. (Multiple wells are seeded for each cell type.)

Second, the cells were allowed to grow to moderate densities. Transformed cells are in contact and non-transformed cells are contact-inhibited under these conditions.

Third, the lipoate derivatives to be tested were added to individual wells. In these experiments each compound was added at two to fourfold above the threshold killing concentration for cancer cells (EXAMPLE 11).

Fourth, cells were monitored over the next several days. For all the blocked lipoate derivatives tested, it was found that each sensitive cancer cell type was efficiently killed, whereas each of four different normal, non-cancer cell types tested were unaffected.

TABLE I

| Cell line | | Bis benzoyl lipoate | Mono acetyl lipoate | bis Acetyl lipoate | bis methyl sucimimido lipoate | bis carbamoyl lipoate | dihydroxy octanoic acid |
|---|---|---|---|---|---|---|---|
| Hep G2 | | + | + | + | + | + | — |
| SW480 | Colon | + | + | + | + | — | — |
| A549 | Lung | + | + | + | + | — | — |
| LnCap | Prostate | + | + | + | + | — | — |
| MCF 7 | Breast | + | + | + | + | — | — |
| HeLa | Cervix | + | + | + | + | — | — |
| B16 | Skin | + | + | + | + | — | — |
| RD | Embryo | + | + | + | + | — | — |
| Saos 2 | Bone | + | + | + | + | — | — |
| NIH 3T3 | ras transformed | + | + | +/− | — | — | — |
| NIH 3T3 | parental | — | — | — | — | — | — |
| MDCK | Kidney | — | — | — | — | — | — |
| NHKC | Skin | — | — | — | — | — | — |

Table 1: Summarized are the responses of cells in culture to killing by example members of the family of blocked lipoate derivatives that are the object of this invention as well as one control compound (dihydroxyoctanoic acid). At right is indicated the specific cell line followed by the tissue of origin of the cell line. Across the top are listed the specific compounds tested. Each blocked lipoate derivative was used at two to fourfold above its threshold-killing concentration. [These concentrations range form 0.15 mM (60 ug/ml or 60 mg/kg) to 2.5 mM (800 ug/ml or 800 mg/kg)(see EXAMPLE 11).] Dihydroxyoctanoic acid was tested up to concentrations of 5 mM (3200 ug/ml or 3200 mg/kg) without detectable effect. "+" indicates that the cells were FIG. 1 shows the results of experiments using the lipoic acid derivatives to selectively kill a number of tumor cell types.

Example 10

In this example, the well-developed culture cell system, NIH-3T3 for testing the lipoic acid derivatives of this invention. NIH-3T3 cells are relatively normal, noncancerous cells. However, if an activated allele of the ras oncogene is introduced into these cells they become highly malignant (cancerous) as assessed by several assays (REFERENCE).

Figure 2:
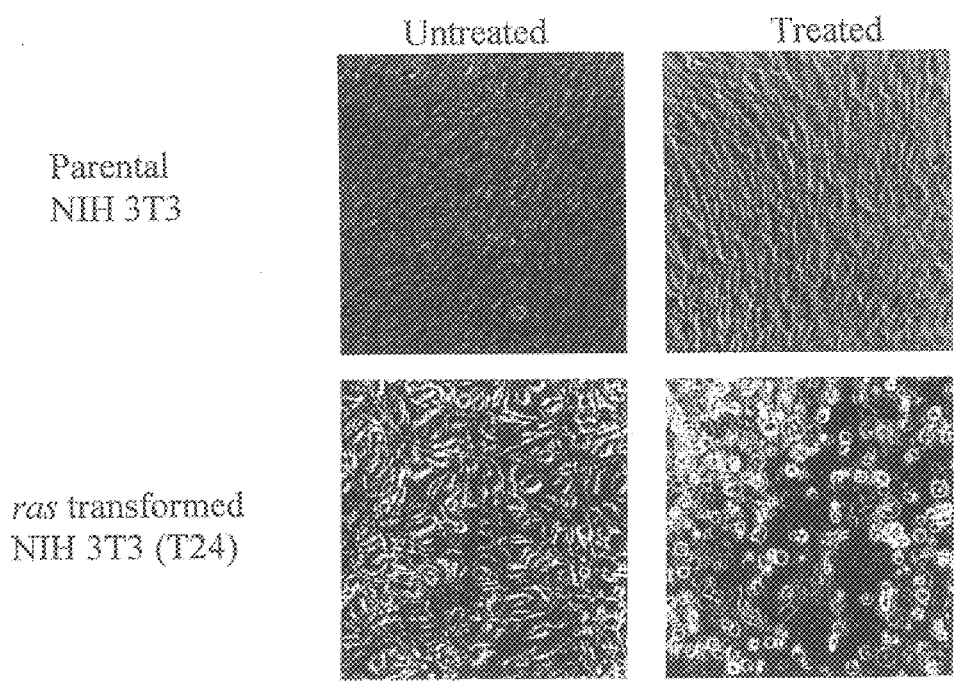
FIG. 2: Shown is the selective killing of ras-transformed NIH3T3 cells in culture by the bis-benzoyl lipoate (120 ug/ml or 120 mg/kg) member of the novel class of compounds that are the object of this invention. See EXAMPLES 9 and 10. The lefthand column describes the non-cancerous (non-transformed) parental NIH3T3 cell line and one of its derivatives (T24) transformed to malignant (cancerous) status by the introduction of an activated form of the ras oncogene. The central column shows these two cell types untreated (control samples) and the rightmost column shows them after ca. 24 hours of bis-benzoyl lipoate treatment. First, the noncancerous parental cells are unaffected by this treatment. Second, in contrast, at 24 hours of treatment ca. 50% of the cancerous (transformed) cells are killed and the remaining cells are rounded and undergoing cell death. See FIGS. 1 and 3 for examples of this characteristic cell rounding and death. By ca. 48 hours of treatment the cancer cells will be almost entirely irradicated (killed) while the corresponding noncancerous parental cells remain unaffected.

Using the procedure described in EXAMPLE 9, the sensitivity to the lipoic acid derivatives of the parental NIH3T3 cells and the ras-transformed T24 derivative of these cells were compared. It was found that the more potent blocked lipoate derivatives (see TABLE 1, EXAMPLE 8) killed the transformed cells very efficiently, while leaving the non-transformed parental cells unaffected. The results are shown in FIG. 2.

Thus, these results provide additional evidence that blocked lipoate derivatives kill cancer cells with high specificity.

Example 11

This example reviews some of the properties shared by the lipoic acid derivatives of the invention.

First, each compound killed cancer cells in culture at or above a relatively narrow, specific concentration range, but not below. The threshold concentrations given below represent the approximate center of this range which extended roughly two to threefold. This killing profile indicated that these compounds saturated one or more cellular processes or targets to produce killing. Below these saturation ranges, sensitive cells survived and grew. They could be removed and replated to grow, apparently indefinitely, under these conditions. In contrast, above these specific concentration ranges of the lipoic acid agent, cell growth was arrested and cell death followed. This was a highly unusual dose/response profile. The threshold killing concentrations (ranges) varied between individual compounds. Examples of these threshold killing concentrations were as follows: bis-benzoyl lipoate (EXAMPLE 3) 60 mg/liter (60 mg/kg), monoacetyl lipoate (EXAMPLE 4) 100 mg/liter (100 mg/kg); bis-acetyl lipoate (EXAMPLE 2) 600 mg/liter (600 mg/kg).

Second, each tested lipoic acid derivative produced specific morphological changes in sensitive target cells throughout an initial 12–24 hour period of treatment. These changes included some rounding, as well as the frequent formation of cell pairs joined by bridge-like structures reminiscent of arrested cytokinesis. These changes were ultimately followed by cell death if treatment was continued. However, these morphological changes were reversed, and the cells recovered, if the lipoate derivative was removed during this initial exposure. As with the dose/response profile of the preceeding paragraph, this reversible induction of morphological change followed by commitment to cell death is highly idiosyncratic. The discovery that this behavior was shown by all tested members of the class of compounds that are the object of this invention was, again, very strong evidence that these compounds are, in fact, a functionally coherent class.

Example 12

This example provides evidence that the lipoic acid derivatives that are the object of this invention kill cancer cells by inducing apoptosis (programmed cell death). Importantly, all tested members had this property. This represented strong additional proof (also see EXAMPLES 8, 9 and 11) that these compounds functioned in the same way. In effect, these compounds apparently induced cancer cells to "commit suicide". Further, induction of apoptosis, rather than necrosis, is a beneficial property for clinical use of these compounds. Under apoptotic conditions, the "suicide" of cancer cells is less disruptive than necrosis of surrounding normal cells.

In order to understand the experiment described in this Example is necessary to review details concerning the specific assay used in the experiments. Nuclear DNA of cells is normally present in the very long molecules making up chromosomes. These very long polymer molecules have only extremely rare free ends. In contrast, after the induction of apoptosis the cell begins to destroy itself and, in the process, introduces an extremely large number of breaks in its DNA in the process of reducing it to its small monomer constituents. The appropriate enzyme—terminal transferase—will add nucleotides to the free ends of DNA molecules. Moreover, this enzyme will use monomers (nucleotides) for this addition reaction that have highly fluorescent groups added to them. Thus, if the nuclei of normal cells—with few free DNA ends—are exposed to terminal transferase and fluorescent monomers very little fluorescence is added to these nuclei. In contrast, when these components are added to the nuclei of cells undergoing apoptosis and very large number of fluorescent monomers are added—to the very many DNA ends that are present—resulting in a massive introduction of fluorescence. The conventional assay based on these properties is referred by the acronym TUNEL.

The following is an example of the experiments demonstrating that the lipoate derivatives that are the objects of this invention induce apoptosis. HeLa cancerous cells were plated in several wells in a tissue culture dish. Some wells (experimentals) were treated with the bis-benzoyl lipoate derivative (EXAMPLE 3) at a concentration ca. twofold higher than the threshold killing concentration (EXAMPLE 11) while other wells (controls) were left untreated. After ca. 20 hours the treated (experimental) cells had begun to undergo death. The experimental and control cells were then fixed, permeabilized and exposed to terminal transferase and fluorescent monomers (nucleotides). This assay demonstrates that the subset of cancer cells actively dying at the moment of assay show the TUNEL fluorescent signal expected of cells undergoing apoptosis. This indicates that all tested members of the lipoic acid compounds that are the object of this invention induce apoptosis in cancer cells.

Figure 3:
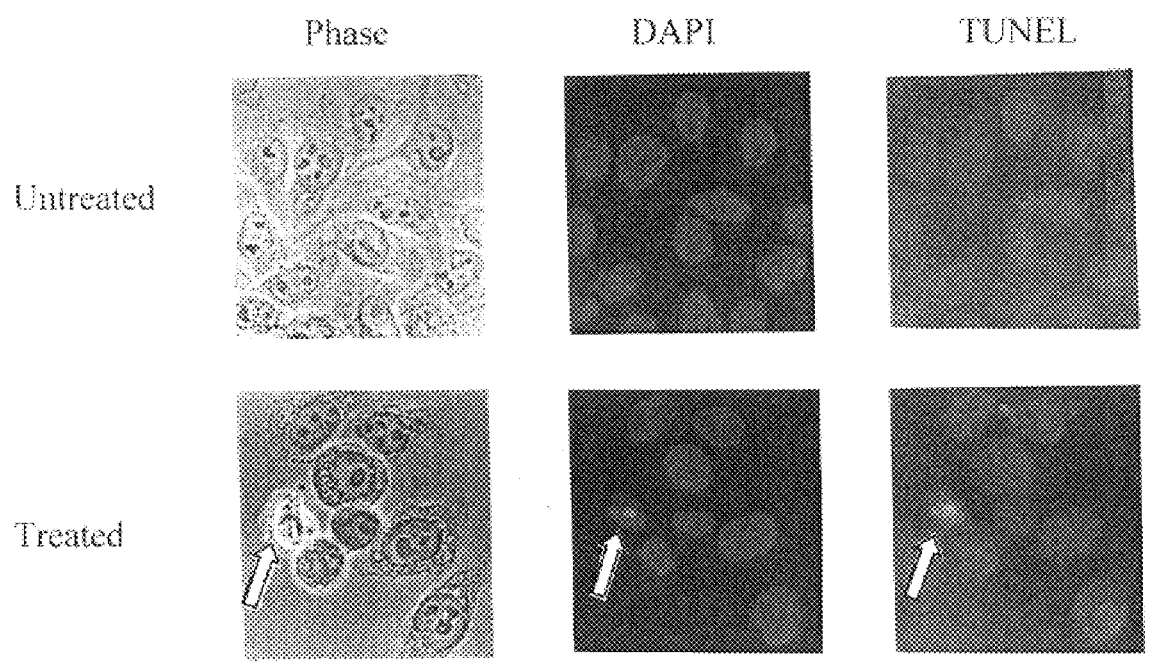
FIG. 3: Shown is the result of a TUNEL assay demonstrating that the bis-benzoyl member of the novel class of compounds that are the object of this invention induces apoptosis (programmed cell death) in cancer cells. In this experiment, HeLa (cervical cancer) cells were treated for ca. 24 hours so that cell death was underway but such that a significant number of live cells remained. All cancer cells are killed within ca. 48–60 hours under these conditions. See EXAMPLE 11. The leftmost photographs show phase contrast light micrographs of the cells. A cell that shows the highly rounded, internally fragmented appearance of a cell undergoing apoptosis is indicated by the arrow. The central photographs show these same cells stained with DAPI and examined by indirect fluorescence microscopy. This reveals DNA showing where cell nuclei are. Note also the characteristic uneven staining of DNA in the apoptotic cell (arrow). The rightmost photographs show the result of the TUNEL assay on these same cells examined by indirect fluorescence microscopy. Note the very low level of staining over most nuclei—reflecting the small number of DNA breaks (see EXAMPLE 11). In contrast, note the very strong fluorescent signal over the apoptotic cell (arrow). This is diagnostic of the large number of DNA breaks characteristic of cells undergoing programmed cell death (apoptosis).

The results of the above experiment are shown in FIG. 3.

Example 13

This section reviews the toxicology in the mouse of the lipoic acid derivatives of this invention. A key issue in assessing the practical clinical usefulness of novel anti-cancer agents is their toxicity to the humans and animals in which they are to be used. To be highly useful, such agents must be relatively innocuous to the human or animal host under conditions where they efficiently kill or inhibit cancer cells. Members of the family of blocked lipoate derivatives show this desirable, essential property as indicated by the following observations.

It has been recognized for many years that even normally occurring, biogenic molecules are toxic if given in sufficiently high doses. Lipoic acid is apparently no exception. At sufficient doses it will kill a mouse. We will refer to this killing henceforth as nonspecific toxicity. The tested members of our novel class of compounds have nonspecific toxicities lower than normal lipoic acid. Moreover, the tested members of this class with highest potency against tumors in cell culture have the lowest nonspecific toxicities.

As a result, the more potent members of this class of compounds can be injected into the animals at doses many times higher than those expected to be sufficient to kill tumor cells in cultured cell systems, with no discernible toxicity to the animal.

Collectively, these results indicate that members of this class of agents can be administered to mice and humans in doses well in excess of those required for treatment of tumors, without significant side effects.

Relevant details of these studies are as follows:

First, lipoic acid itself (D,L racemic mixture) has an LD-50 of ca. 100 mg/kg body weight in mice. (All studies described in this section were carried out by intraperitoneal (IP) injection into C57/BL mice.)

Second, nonspecific toxicity in the bis-acyl lipoic acid derivative was found producing an LD-50 of ca. 500 mg/kg with a maximum well-tolerated dose of ca. 200 mg/kg. Note, also, that this is significantly lower nonspecific toxicity than normal lipoate. [Note that the nonspecific toxicity of this and all other lipoate compounds tested was acute—death of the animal occurs within minutes of IP injection. It, thus, appeared to be unrelated to the cell death occurring over a period of days in cancer cells treated in culture with blocked lipoate derivatives (See, EXAMPLES 8–12).

Third, the bis-benzyl lipoic acid derivative had an LD-50 of ca. 1000 mg/kg of body weight with a maximum well-tolerated dose of ca. 500 mg/kg. This was significantly lower toxicity than that of bis-acetyl lipoate (above) and much lower than normal lipoate.

Fourth, on the basis of these results the following calculations were done: Total animal mass was ca. 70% water. This was distributed as follows. Ca. 50% of adult mass was intracellular water, ca. 15% of total mass was non-blood extracellular fluid (generally referred to as "interstitial fluid") and ca. 5% of total mass was blood. This led to the following projected sequence.

Ca. 500 mg/kg of the bis-benzyl derivative was injected into the peritoneal cavity of a mouse. This material was very rapidly taken up into the blood. The effective dose of the bis-benzyl derivative in cell culture was 60 ug/ml or 60 mg/kg (see, EXAMPLES 8 and 11). It was expected that this IP injection would rapidly equilibrate with blood, producing concentrations transiently approaching 10,000 mg/kg or ca. 167 times the effective concentration of this agent in the blood. This was further expected to equilibrate with interstitial fluid producing concentrations approaching 2500 mg/kg or ca. 42 times the effective concentration in this fluid. This then equilibrated with the total body fluids to produce concentrations approaching 715 mg/kg or ca. 12 times the effective dose in total body fluids.

In sum, these results have two key implications. First, they indicate that effective concentrations could be readily achieved of the more potent members of this class of agents—including bis-benzoyl lipoate—which were expected to be sufficient to kill cancer cells in the animal while leaving the animal otherwise apparently unaffected. This combination of low nonspecific toxicity and high specific toxicity for tumor cells was striking and indicated that this class of agents had high clinical potential. Second, the relative properties of the bis-acetyl and bis-benzoyl members of the lipoic acid derivative family illustrated this point. Both derivatives had specific anti-cancer activity that normal lipoate did not have, while simultaneously having lower levels of nonspecific toxicity. Further, a similar relationship was seen among the blocked lipoate derivatives as follows. Bis-benzoyl lipoate simultaneously had lower nonspecific toxicity and much higher anti-cancer potency than does the bis-acetyl derivative. This, and similar results clearly demonstrated that anti-cancer activity and nonspecific toxicity vary independently.

Example 14

The discoveries described above indicate that one should be able to kill cancer cells without harming the human or animal under treatment using members of the novel class of compounds that are the objects of this invention (see, especially, EXAMPLES 8 and 13). In this example, the results of studies in mice which support this expectation. Relevant results are as follows.

The B-16 melanoma strain was introduced either subcutaneously or intraperitoneally into individuals of the C57/BL syngeneic mouse strain (7). When left untreated such mice develop massive tumors in the immediate area of injection as well as secondary metastases throughout the animal—including in the liver and the lungs. These malignant growths result in the early death of the animals. Moreover, the resulting malignant growths are made up of darkly pigmented malignant melanocytes—making their assessment convenient and highly reliable. We will henceforth refer to this as the "B-16 system".

Using the B-16 system we have used the bis-benzoyl and bis-acetyl lipoate members to demonstrate that members of the novel class of compounds that are the object of this invention have the anti-cancer efficacy expected based on the discoveries described in preceding EXAMPLES. The relevant results are as follows.

First, a group of mice were injected IP with B-16 cells. The injected group was divided at random into two equal subsets. One subset (experimental) was injected IP twice a day with 100 mg/kg of the bis-benzoyl lipoate member of the compound class in 200 ul of 10% ethanol. [See EXAMPLES 3, 8 and 11 for descriptions of bis-benzoyl lipoate.] The second subset (control) was injected with 200 ul of 10% ethanol alone.

After 16 days, the animals were examined—including by dissection where appropriate. The control animals had numerous, massive IP tumor masses. In contrast, the corresponding experimental animals had substantially reduced tumor number and mass—less than 30–50% as much mass as the control sample.

Second, a group of animals were injected at a subcutaneous site with B-16 cells. After 6–8 days, large, spherical, easily palpable tumors (ca. 3–5 mm in diameter) were observed at the site of initial cell injection. As this time, one group of animals (experimentals) began a twice-daily series of injections of the bis-acetyl lipoate derivative (100 mg/kg in 100 ul of isotonic saline) and a second set (controls) of corresponding injections of the saline solvent alone. [See EXAMPLES 2, 8 and 11 for the details of bis-acetyl lipoate derivative.] In the experimental animals—but not the controls—we commonly observed a palpable softening and apparently partial liquification of the tumor mass followed by a stabilization or a reduction in size. This indicates that the bis-acetyl derivative is producing significant cell death in these tumors under these circumstances.

Third, in several animals subcutaneous tumors were produced as in the preceding paragraph. After the tumors had grown to visible, palpable size, these animals received both a twice daily IP (systemic) dose of 50 mg/kg of bis-benzoyl lipoate as well as a twice daily direct injection a second dose of the same volume directly into the tumor mass. These animals apparently showed an especially robust response, including one case in which the tumor mass shrank dramatically and largely or entirely disappeared over the course of treatment.

In summary, these results clearly indicate that the bis-benzoyl and bis-acetyl lipoate derivatives have the expected anti-cancer efficacy and specificity in the intact animal. Based on these results, those skilled in the art could adjust the doses and dosing regimes to produce partial or complete control and/or elimination of these tumors in these animals.

Example 15

One likely mechanism of action of the blocked lipoate derivatives that are the object of this invention is that they inhibit PDC specifically in cancer cells resulting in loss of mitochondrial membrane polarization and consequent induction of apoptosis in cancer cells. It is anticipated that blocked lipoate derivatives might interact synergistically with other agents that either inhibit mitochondrial energy metabolism and/or induce apoptosis in some other fashion.

This was tested in this Example with dichloroacetate (henceforth abbreviated DCA)(8). This compound is a pyruvate analog. As such, one of its effects is expected to be competitive inhibition of PDC. It was found that this compound interacts synergistically with blocked lipoate derivatives as expected. A relevant experimental observation is as follows.

HeLa cells were plated at moderate densities and allowed to attach and grow for ca. 24 hours in a series of wells in a multi-well tissue culture plate. To individual wells of the first subset (control) were added bis-acetyl lipoate, mono-acetyl lipoate or bis-benzoyl lipoate—each at ca. twofold above the threshold killing dose (EXAMPLE 11). To an equivalent (experimental) subset of wells were added these same compounds at the same dose together with the simultaneous addition of DCA to 5 mM final concentration. We find that the cells of the experimental subset are killed approximately twice as rapidly as in the control subset.

This was a striking effect. At 24 hours post treatment the experimental group was almost entirely killed, whereas a similar level of nearly complete killing was not seen until ca. 48 hours in the control subset.

Based on experimental observations of this sort, it is likely that these lipoate derivatives of this invention will interact synergistically with other metabolic inhibitors and/or other chemotherapeutic agents to kill cancer cells more efficiently. Indeed, one effective clinical application of the novel compounds that are the object of this invention may be in concert with other agents.

REFERENCES (1) Baggetto, L G. 1992. Deviant energetic metabolism of glycolytic cancer cells. Biochemie 74: 959–974.
(2) Garrett, R H and Grisham, C M. 1995. Biochemistry. New York: Saunders College Publishing.
(3) Dvorak, H F. 1986. Tumors: wounds that do not heal. Similarities between tumor stroma generation and wound healing. New England Journal of Medicine 315: 1650–1659.
(4) Whalen, G F. 1990. Solid tumors and wounds: transformed cells misunderstood as injured tissue? Lancet 136: 1489–1492.
(5) Patel, M S and Roche, T E. 1990. Molecular biology and biochemistry of pyruvate dehydrogenase complexes. FASEB Journal 4: 3224–3233.
(6) Johnson, L V, et al. 1980. Proceedings of the National Academy of Sciences, USA 77: 990–994.
(7) Fidler, I. J., Gersten, D. M. and Budman, M. B. 1976. Characterization in vivo and in vitro of tumor cells selected for resistance to syngeneic lymphocyte-mediated toxicity. Cancer Res. 36: 3160–3165.
(8) Stacpoole, P. W., Henderson, G. N., Yan, Z., Cornett, R. and James, M. O. 1998. Pharmacokinetics, metabolism and toxicology of dichloroacetate. Drug Metabolism Reviews. 30: 499–539.
(9) Hill, S. A., Wilson, S., Chamber, A. F. 1988. Clonal heterogeneity, experimental metastatic ability, and p21 expression in H-ras-transformed NIH 3T3 cells. J. Nat'l Cancer Inst. 80: 484–90.

We claim:

1. A composition comprising the formula:

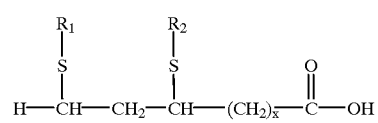

wherein:
x is 0–16
$R_1$ and $R_2$ are independently acyl $R_3C(O)$—;
wherein $R_3$ is an alkyl or aryl group; alkyl $C_nH_{2n+1}$; alkenyl $C_mH_{2m-1}$; alkynyl $C_mH_{2m-3}$; aryl, alkyl sulfide $CH_3(CH_2)_n$—S—; imidoyl $CH_3(CH_2)_nC(=NH)$—; and semiacetal $R_4CH(OH)$—S—;
wherein $R_4$ is $CCl_3$ or COOH; and wherein n is 0–10 and m is 2–10.

2. A composition comprising the formula:

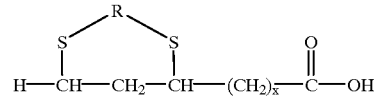

wherein:
x is 0–16; and
R is a non-palladium metal chelate.

3. The composition of claim 1 wherein $R_1$ and $R_2$ are acetyl groups.

4. The composition of claim 1 wherein $R_1$ and $R_2$ are benzoyl groups.

5. The composition of claim 1 wherein the alkene group is selected from the group consisting of propylene, 2,3-dimethyl-2-butene and heptene.

6. The composition of claim 1, wherein the alkyne is selected from the group consisting of acetylene, propyne and octyne.

7. The composition of claim 1, wherein the aromatic group is a benzene or benzene derivative.

8. The composition of claim 1, wherein the alkyl group is cyclopropane.

9. The composition of claim 1, wherein the alkene group is cyclopentene.

10. A pharmaceutical composition comprising a composition of any of claims 7 through 9 and a pharmaceutically acceptable carrier.

11. The pharmaceutical composition of claim 10 further comprising a second reagent.

12. The pharmaceutical composition of claim 11 wherein the second reagent is dichloroacetate.

13. A pharmaceutical composition comprising a lipoic acid derivative and a pharmaceutically acceptable carrier.

14. The pharmaceutical composition of claim 13, wherein the lipoic acid derivative is a lipoic acid-metal complex, wherein metal is not palladium.

15. The pharmaceutical composition of claim 14, wherein of the lipoic acid-metal complex is provided in the form of a solution in a therapeutically effective amount-sufficient to obtain a concentration at or above 10 μM.

16. The pharmaceutical composition of claim 14, wherein the metal is selected from the group consisting of platinum, nickel, silver, rhodium, cadmium, gold or cobalt.

17. The pharmaceutical composition of claim 13, wherein one or both of the lipoic acid thiols are oxidized to sulfate groups.

18. A method of inhibiting proliferation of diseased cells by contacting the diseased cells with an effective amount of a reagent that inhibits PDC specifically in said diseased cells.

19. The method according to claim 18, wherein the inhibition of said diseased cell proliferation is irreversible.

20. The method according to claim 18, wherein the reagent is a lipoic acid derivative.

21. The method according to claim 20, further comprising contacting tumor cells with an effective amount of said lipoic acid derivative to kill said tumor cells.

22. The method of according to claim 18, comprising contacting cells containing a disease selected from the group consisting of eubacterial, archeal, fungal, plant, algal or protozoan parasites for the purpose of inhibiting PDC function specifically in said diseased cells.

23. A method of treating a disease characterized by disease cells that are sensitive to lipoic acid derivatives comprising administering a therapeutic amount of a lipoic acid compound of the formula:

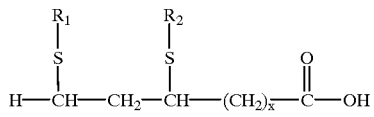

wherein:

x is 0–16

$R_1$ and $R_2$ are independently acyl $R_3C(O)$—;

wherein $R_3$ is an alkyl or aryl group; alkyl $C_nH_{2n+1}$; alkenyl $C_mH_{2m-1}$; alkynyl $C_mH_{2m-3}$; aryl, alkyl sulfide $CH_3(CH_2)_n$—S—; imidoyl $CH_3(CH_2)_nC(=NH)$—; and semiacetal $R_4CH(OH)$—S—;

wherein $R_4$ is $CCl_3$ or COOH; and wherein n is 0–10 and m is 2–10.

24. A method of treating a disease characterized by disease cells that are sensitive to lipoic acid derivatives comprising administering a therapeutic amount of a lipoic acid compound of the formula:

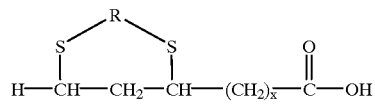

wherein:

x—0–16; and

R is a no-palladium metal chelate.

25. The method of claims 23 or 24 wherein the disease comprises a neoplastic disease.

26. The composition according to claim 1 wherein one of $R_1$ and $R_2$ is substituted by a hydrogen.

27. The method according to claim 23 wherein one of $R_1$ and $R_2$ is substituted by a hydrogen.

* * * * *

UNITED STATES PATENT AND TRADEMARK OFFICE
CERTIFICATE OF CORRECTION

| | |
|---|---|
| PATENT NO. | : 6,331,559 B1 |
| APPLICATION NO. | : 09/427477 |
| DATED | : December 18, 2001 |
| INVENTOR(S) | : Paul M. Bingham et al. |

It is certified that error appears in the above-identified patent and that said Letters Patent is hereby corrected as shown below:

ABSTRACT

Line 2, "target and kill" should read --targets and kills--; and
    Line 3, "cells," should read --cells--.

COLUMN 1

Line 11, "target" should read --targets--;
    Line 12, "kill tumor cells," should read --kills tumor cells--;
    Line 22, "glycolytic" should read --the glycolytic--;
    Line 52, "example prostrate" should read --example, prostate--; and
    Line 62, "example" should read --example,--.

COLUMN 2

Line 28, "target and kill" should read --targets and kills--;
    Line 47, "comprise" should read --comprises--;
    Line 49, "comprise" should read --comprises--;
    Line 59, "x is 0-16" should read --x is 0-16;--;
    Lines 60-65, "$R_1$ and $R_2$ are independently acyl $R_3C(O)$; wherein $R_3$ is an alkyl or aryl group; alkyl $C_nH_{2n+1}$; alkenyl $C_mH_{2m-1}$; alkynyl $C_mH_{2m-3}$; aryl, alkyl sulfide $CH_3(CH_2)_n$-S-; imidoyl $CH_3(CH_2)_nC(=NH)$-; and semiacetal $R_4CH(OH)$-S-; wherein $R_4$ is $CCl_3$ or COOH; and wherein n is 0-10 and m is 2-10." should read --$R_1$ and $R_2$ are independently acyl $R_3C(O)$, wherein $R_3$ is an alkyl or aryl group; alkyl $C_nH_{2n+1}$; alkenyl $C_mH_{2m-1}$; alkynyl $C_mH_{2m-3}$; aryl; alkyl sulfide $CH_3(CH_2)_n$-S-; imidoyl $CH_3(CH_2)_nC(=NH)$-; and semiacetal $R_4CH(OH)$-S-, wherein $R_4$ is $CCl_3$ or COOH; and n is 0-10 and m is 2-10.--
    Line 66, "comprise" should read --comprises--.

COLUMN 3

Line 30, "invention," should read --invention--.

COLUMN 4

Line 18, "irradicated (killed)" should read --eradicated (killed),--.

UNITED STATES PATENT AND TRADEMARK OFFICE
CERTIFICATE OF CORRECTION

PATENT NO. : 6,331,559 B1
APPLICATION NO. : 09/427477
DATED : December 18, 2001
INVENTOR(S) : Paul M. Bingham et al.

It is certified that error appears in the above-identified patent and that said Letters Patent is hereby corrected as shown below:

COLUMN 5

Line 12, "alkyl" should read --an alkyl--;
Line 18, "a" should be deleted;
Line 21, "through an" should read --through a--;
Line 28, "through an" should read --through a--;
Line 34, "CnH$_{2n-2}$" should read --alkynyl C$_n$H$_{2n-3}$--;
Line 47, "through an" should read --through a--;
Line 53, "0-9)" should read --0-9--;
Line 56, "to 1-10]" should read --to, 1-10--; and
Line 68, "respectively" should read --respectively.--.

COLUMN 6

Line 40, "N-ethylmalemide" should read --N-ethylmaleimide--; and
Line 63, "cobalt bromide," (second occurrence) should be deleted.

COLUMN 7

Line 7, "with" should read --with a--.

COLUMN 8

Line 9, "i.e." should read --i.e.,--.

COLUMN 9

Line 24, "is" should read --are--;
Line 36, "Sodium" should read --sodium--;
Line 54, "6,8-bisacetylmercaptooctanoic" should read --6,8-bisacetylmercaptooctanoic acid--;
Line 56, "-lipoic" should read --lipoic--; and
Line 63, "accompished as follows." should read --accomplished as follows:--.

COLUMN 10

Line 28, "6,8-Bisacetylinercaptooctanoic" should read --6,8-Bisacetylmercaptooctanoic--; and
Line 65, "example" should read --example of--.

UNITED STATES PATENT AND TRADEMARK OFFICE
CERTIFICATE OF CORRECTION

PATENT NO. : 6,331,559 B1
APPLICATION NO. : 09/427477
DATED : December 18, 2001
INVENTOR(S) : Paul M. Bingham et al.

It is certified that error appears in the above-identified patent and that said Letters Patent is hereby corrected as shown below:

COLUMN 11

Line 36, "6,8-Bisbenzoylmercaptooctanoic" should read --6,8-bisbenzoylmercaptooctanoic--;
      Line 48, "Silica Gel" should read --silica gel--; and
      Line 52, "step" should read --steps--.

COLUMN 12

Line 13, "450" should read --45°--;
      Line 22, "450" should read --45°--;
      Line 27, "Silica Gel" should read --silica gel--;
      Line 33, "the product" should be deleted;
      Line 56, "vigorously" should read --vigorous--; and
      Line 64, "P2O5" should read --$P_2O_5$--.

COLUMN 13

Line 25, "MgSO4" should read --$MgSO_4$--; and
      Line 49, "6 8-Biscarbamoylmethylmercaptooctanoic" should read --6,8-Biscarbamoylmethylmercaptooctanoic--.

COLUMN 14

Line 14, "6,8-Bismercaptoocatanoic" should read --6,8-Bismercaptooctanoic--;
      Line 25, "MgSO4" should read --$MgSO_4$--;
      Line 26, "Silica" should read --silica--; and
      Line 41, "6 8-Dihydroxyoctanoate" should read --6,8-Dihydroxyoctanoate--.

COLUMN 15

Line 15, "derivative" should read --derivatives--; and
      Line 18, "cells" should read --cell--.

COLUMN 16

Line 61, "for" should read --was used for--.

COLUMN 17

Line 31, "mg/kg);" should read --mg/kg),--; and
      Line 66, "Example" should read --Example, it--.

UNITED STATES PATENT AND TRADEMARK OFFICE
CERTIFICATE OF CORRECTION

PATENT NO. : 6,331,559 B1
APPLICATION NO. : 09/427477
DATED : December 18, 2001
INVENTOR(S) : Paul M. Bingham et al.

It is certified that error appears in the above-identified patent and that said Letters Patent is hereby corrected as shown below:

COLUMN 18

Line 16, "very" should read --a very--; and
Line 18, "resulting in" should be deleted and "fluorescence" should read --fluorescence results--.

COLUMN 19

Line 18, "benzyl" should read --benzoyl--;
Line 30, "benzyl" should read --benzoyl--; and
Line 33, "benzyl" should read --benzoyl--.

COLUMN 20

Line 4, "which" should be deleted.

COLUMN 22

Lines 13-18,
"x is 0-16
$R_1$ and $R_2$ are independently acyl $R_3C(O)$;
wherein $R_3$ is an alkyl or aryl group; alkyl $C_nH_{2n+1}$;
alkenyl $C_mH_{2m-1}$; alkynyl $C_mH_{2m-3}$; aryl, alkyl sulfide $CH_3(CH_2)_n$-S-; imidoyl $CH_3(CH_2)_nC(=NR)$-;
and semiacetal $R_4CH(OH)$--S-;" should read
--x is 0-16;
$R_1$ and $R_2$ are independently acyl $R_3C(O)$, wherein $R_3$ is
an alkyl or aryl group; alkyl $C_nH_{2n+1}$; alkenyl $C_mH_{2m-1}$;
alkynyl $C_mH_{2m-3}$; aryl; alkyl sulfide $CH_3(CH_2)_n$-S-;
imidoyl $CH_3(CH_2)_nC(=NH)$-; and semiacetal $R_4CH(OH)$--S-;--.
Line 35, "alkene" should read --alkenyl--;
Line 38, "alkyne" should read --alkynyl--;
Line 41, "aromatic" should read --aryl--;
Line 45, "alkene" should read --alkenyl--;
Line 52, "11" should read --11,--;
Line 60, "of" (first occurrence) should be deleted; and
Line 61, "amount-sufficient" should read --amount sufficient--.

UNITED STATES PATENT AND TRADEMARK OFFICE
CERTIFICATE OF CORRECTION

PATENT NO. : 6,331,559 B1 Page 5 of 5
APPLICATION NO. : 09/427477
DATED : December 18, 2001
INVENTOR(S) : Paul M. Bingham et al.

It is certified that error appears in the above-identified patent and that said Letters Patent is hereby corrected as shown below:

COLUMN 23

Lines 28-29,
"x is 0-16
$R_1$ and $R_2$ are independently acyl $R_3C(O)$;"     should read
--x is 0-16;
$R_1$ and $R_2$ are independently acyl $R_3C(O)$, wherein $R_3$ is--.

COLUMN 24

Lines 1-4,
"wherein $R_3$ is an alkyl or aryl group; alkyl $C_nH_{2n+1}$;
alkenyl $C_mH_{2m-1}$; alkynyl $C_mH_{2m-3}$; aryl, alkyl sulfide
$CH_3(CH_2)_n$-S-; imidoyl $CH_3(CH_2)_nC(=NH)$-;
and semiacetal $R_4CH(OH)$--S-;"     should read
-- an alkyl or aryl group; alkyl $C_nH_{2n+1}$; alkenyl $C_mH_{2m-1}$;
alkynyl $C_mH_{2m-3}$; aryl; alkyl sulfide $CH_3(CH_2)_n$-S-;
imidoyl $CH_3(CH_2)_nC(=NH)$-; and semiacetal $R_4CH(OH)$--S-;--
Line 20, "x-0-16" should read --x is 0-16--;
Line 21, "no" should read --non--;
Line 22, "24" should read --24,--;
Line 24, "1" should read --1,--; and
Line 26, "23" should read --23,--.

Signed and Sealed this

Twelfth Day of December, 2006

JON W. DUDAS
*Director of the United States Patent and Trademark Office*